US00PP33878P2

(12) United States Plant Patent
Hansen

(10) Patent No.: US PP33,878 P2
(45) Date of Patent: Jan. 18, 2022

(54) ***LEUCANTHEMUM* PLANT NAMED 'MARSHMALLOW'**

(50) Latin Name: ***Leucanthemum* x *superbum***
Varietal Denomination: Marshmallow

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/300,511

(22) Filed: Jul. 27, 2021

(51) Int. Cl.
*A01H 5/02* (2018.01)
*A01H 6/14* (2018.01)

(52) U.S. Cl.
USPC ..... Plt./285

(58) Field of Classification Search
USPC ..... Plt./285
See application file for complete search history.

*Primary Examiner* — Susan McCormick Ewoldt

(57) ABSTRACT

The new Shasta daisy plant, *Leucanthemum* 'Marshmallow', is a sturdy plant with green serrated foliage and stiff stems. The numerous freely-flowering inflorescences producing buds beginning with light yellow ray florets developing to near white. The outer ray florets are lanceolate to linear and emarginate and the inner ray florets are mostly laciniate and retain their yellow coloration longer. The center disk florets are yellow. Flowering repeats into fall if deadheaded. The new plant is useful in the landscape as a long-flowering border, in mass, as accent plants and containerized for patio or indoor use, or as a cut flower.

1 Drawing Sheet

Botanical classification: *Leucanthemum* x *superbum* (Bergmans ex J.W.Ingram) D.H.Kent.

Variety denomination: 'Marshmallow'.

STATEMENT REGARDING PRIOR DISCLOSURES UNDER 37 CFR 1.77(B)(6)

The first non-enabling disclosure of the claimed plant was made by Walters Gardens, Inc. on Dec. 1, 2020 in the form of a website brief description and photograph followed by a short description and photograph in the "Walters Gardens 2021-2022 Catalog" by Walters Gardens, Inc first distributed on May 21, 2021. The first enabling disclosure of a sales of the claimed plant was on Aug. 3, 2020 by Walters Gardens, Inc. Walters Gardens, Inc. obtained the new plant and information about the new plant directly from the inventor. No plants of *Leucanthemum* 'Marshmallow' have been sold, in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The original *Leucanthemum* x *superbum*, or Shasta daisies, were bred by Luther Burbank in the late 1800's as a cross between *Leucanthemum maximum* (Ramond) DC. with *Leucanthemum lacustre* (Broth.) Samp. and *Nipponanthemum nipponicum*. The new plant, *Leucanthemum* 'Marshmallow' originated from a planned breeding program of the inventor at a wholesale perennial nursery in Zeeland, Mich., USA. The new *Leucanthemum* was a single plant selected from a group of seedlings from a cross on Jul. 15, 2015 between 'Sante' U.S. Plant Pat. No. 19,829 and 'Banana Cream' U.S. Plant Pat. No. 23,181. The individual plant that eventually became 'Marshmallow' was first evaluated in the summer of 2016 and originally given the breeder number 15-1-3 through the subsequent evaluations.

The present invention relates to a new and distinct cultivar of Shasta daisy botanically known as *Leucanthemum* x *superbum* and hereinafter referred to by the cultivar name 'Marshmallow' or the new plant.

Asexual reproduction of the new cultivar initially by division and later by basal cuttings and shoot tip tissue culture at the same nursery in Zeeland, Mich. as late summer or early fall of 2017 has demonstrated that the new cultivar reproduces true to type with all of the characteristics of the original plant retained through successive generations of asexual propagation.

BRIEF SUMMARY OF THE INVENTION

The new plant, *Leucanthemum* 'Marshmallow', is most closely compared to *Leucanthemum* 'Sante' and 'Banana Cream' in flower and *Leucanthemum* and 'Cream Puff' U.S. Plant Pat. No. 30,074, 'Snowcap' (not patented) and 'Whoops-a-Daisy' U.S. Plant Pat. 27,259 in compact habit, 'Ice Star' (not patented), 'Fiona Coghill' (not patented), 'Double Angel' (not patented).

In test trials in Zeeland, Mich., 'Cream Puff' has a slightly shorter habit and has flowers that are less double and the ray floret ligules are less dissected. Compared with 'Whoops-a-Daisy' the new plant is slightly smaller in habit and the ray floret ligules of 'Marshmallow' are more numerous, have more yellowish coloration and are more laciniate. 'Snowcap' has smaller single inflorescences and taller habit. 'Ice Star' is much taller in habit with the ray florets not laciniate and droop in maturity. 'Fiona Coghill' is much taller in habit with the flower stem arching outwardly and the ray florets not laciniate. 'Double Angel' has a much taller habit, more drooping outer ray florets, and the inner ray florets are smaller and not as laciniate.

'Sante' has smaller, flatter and less dome-shaped inflorescences with less yellow ray florets. 'Banana Cream' has a more single inflorescence with ray florets that are more yellow and slightly taller habit.

*Leucanthemum* 'Marshmallow' differs from all cultivars known to the inventor in the following combined traits:

1. Sturdy, compact, dense, mounded plants with green serrated foliage and stiff stems;
2. Inflorescence of numerous double capitulum.
3. Outer row of ray florets with ligules lanceolate to linear and emarginate;
4. Inner rows of ray florets with ligules tending to be more laciniate;
5. Center disk florets of yellow;
6. Ray floret ligules beginning light yellow and lightening to near white;
7. Freely flowering habit and repeating if deadheaded.

BRIEF DESCRIPTION OF THE PHOTOGRAPHS

The photographs of 'Marshmallow' demonstrate the overall appearance and landscape qualities of the new plant, including the unique traits planted in a full-sun trial garden in Zeeland, Mich. The colors are as accurate as reasonably possible with color reproductions. Ambient light spectrum, source, direction and temperature may cause the appearance of minor variation in color.

DETAILED BOTANICAL DESCRIPTION

Figure 1:
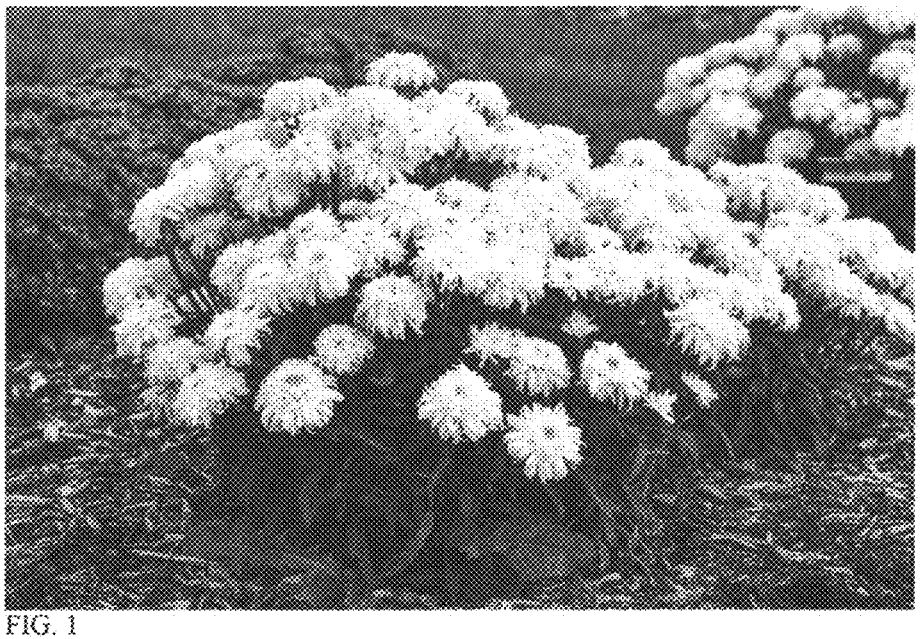
FIG. 1 shows a two-year-old new plant at peak flowering with inflorescences covering the plant from nearly top to ground.
Figure 2:
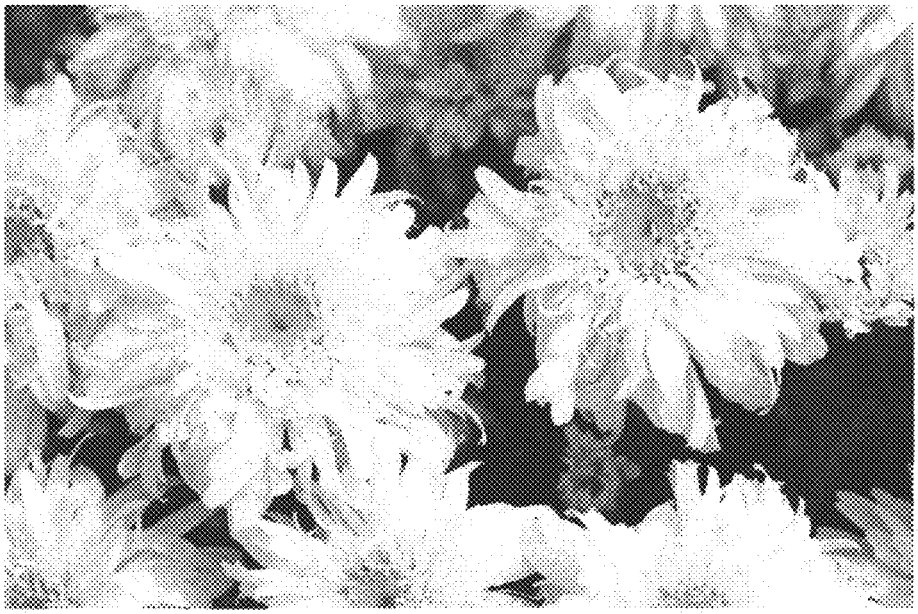
FIG. 2 shows a close-up of the inflorescence and the buds.

The following descriptions and color references are based on the 2015 edition of The Royal Horticultural Society Colour Chart except where common dictionary terms are used. The new plant has not been observed in all possible environments and conditions. The phenotype of *Leucanthemum* 'Marshmallow' may vary with different growing conditions such as changes in temperature, light intensity, water availability, fertility, but without change in the genotype.

The plants used for description purposes were one year old and were grown in Zeeland, Mich. in a full-sun, loamy-sand trial plot environment with supplemental water and limited fertilizer as needed. Summer temperatures range from night lows of about 10° C. to daytime highs of about 34° C. Measurements and numerical values represent averages of trial plants.

Botanical classification: *Leucanthemum* x *superbum;*

Parentage: Female is 'Sante', male parent is 'Banana Cream';

Habit: Herbaceous perennial with about 16 branched stems arising from rhizome base; each stem having three to eight inflorescences each, rarely two; about 30 cm tall and 41 cm across with rounded top and sides;

Roots: Fibrous, thin, heavily branched; root color nearest RHS 155D depending on soil type;

Propagation: Tip cuttings or tissue culture; about two weeks to produce roots from cutting; about 33 weeks to finish to flower in 3.8 liter pot depending on season;

Stems: About 16 main stems per plant; strong; mostly upright; canaliculated; sparsely hispidulous; terete, hollow in distal portion; 10.0 mm diameter at base; to 28 cm tall; about 13 nodes before flowers; average internode length about 1.0 cm;

Stem color: Nearest RHS 137B;

Axillary branches: Three to eight, rarely two per main stem; between 6.0 to 12.0 cm long and 4.0 to 6.0 mm diameter; at angles of about 30° from main stem; side flowers rising above initial flower;

Axillary branch color: Nearest RHS 137B;

Leaves: Lanceolate to linear; apex acute; base attenuate; alternate; sparsely puberulent adaxial and abaxial; margin serrate and ciliolate with average about twelve teeth per side, and size average about 2.0 mm long and 3.0 mm wide; adaxial and abaxial nearly microscopically micro-ciliolate; lowest leaves about 13.0 cm long and 4.2 cm wide, average about 9.0 cm long and 3.2 cm wide; no fragrance detected;

Leaf color: Young adaxial nearest RHS 146A, abaxial between RHS 146B and RHS 146C; mature adaxial nearest RHS 137A, abaxial between RHS 146A and RHS 146B;

Veins: Anastomosing; glabrescent adaxial and abaxial; adaxial slightly raised, abaxial midrib costate and secondary veins smooth;

Vein color: Adaxial midrib nearest RHS 145A proximally and distal midrib and secondary veins nearest RHS 137A; abaxial midrib nearest RHS 146C and secondary veins nearest RHS 137A;

Inflorescence: Up to 21 cm and flowering in the upper 17 cm;

Flower: Capitate, about 30 per plant at one time; primary flower 7.0 cm across and 4.2 cm tall; comprising one outer row of larger ray florets, 3 to 8 rows of smaller laciniate ray florets and mixed within the central disk florets; individual flower lasting about three weeks on or cut from plant; upright;

Fragrance: No fragrance detected;

Flowering period: Early summer (late June) to early autumn in Michigan if deadheaded;

Peduncle: Strong, stiff; sparsely hispidulous to puberulent; cylindrical; longitudinally fluted; 6.0 to 25.0 cm long and about 9.0 mm diameter at base; upwardly;

Peduncle color: Nearest RHS 146B;

Bud: With ray florets still vertical — oblong globose, 1.6 cm across ray florets and 1.5 cm from base of phyllaries to apex of capitulum;

Bud color: Adaxial and abaxial ray floret ligule coloration nearest RHS 4C; phyllaries nearest RHS 138A in center and margin nearest RHS 196D;

Floret type: Variable; ray florets on the exterior, mostly disk florets toward flower center; in between mixture of ray and disk florets;

Larger outer ray florets: About 20 per flower; arranged around outer perimeter of capitulum in single row; ligules glabrous adaxial and abaxial, base attenuate rolled into tube, apex emarginate with typically two notches indented to about 1.0 mm, margin entire; to about 38.0 long and 7.0 mm wide, arcuate to 270° below flower;

Inner ray florets: About 450 to 550; ligules variable, laciniate, typically with two to four lobes (rarely six) cut to within about 2.0 mm from ovary, spreading to about 22.0 mm wide; lobes linear and frequently divergent, 1.0 mm to 5.0 mm wide and to about 29.0 mm long, deep at apex to laciniate with three lobes cleft to 24.0 mm deep; base attenuate, margin entire; broader lobes with emarginate apices, narrower lobes with acute apices;

Disk florets: To about 400 to 500 per flower, concentrated near center of capitulum but mixed within inner ray florets; combined flower disk variable, to about 12.0 mm across and about 10.0 mm tall; individual floret about 7.0 mm tall and 2.0 mm wide, five tepals, about 7.0 mm long; with acute apex, fused in basal 6.0 mm;

Ray floret color: Mature adaxial and abaxial tepals nearest RHS NN155C and basal 5.0 mm nearest RHS 145A, young tepals adaxial and abaxial between RHS 1D and RHS 1C with base nearest RHS 145B;

Inner ray floret color: As ligules are first expanding adaxial and abaxial between RHS 1D and RHS 1C, apices nearest RHS 3B and with base nearest RHS 145D; mature ligule adaxial and abaxial nearest RHS NN155D with base between RHS 145A and RHS 146D;

Disk floret color: Young adaxial and abaxial tepal nearest RHS 12A distally, center nearest RHS 145C and nearest RHS 145D proximally; mature adaxial and abaxial tepal distally nearest RHS 14C, center nearest RHS 157B and base nearest RHS 199D;

Androecium: Five stamens connate around style;

*Anther*.—Five; connate into tube; about 1.0 mm long and less than one mm wide, rudimentary in ray florets, functional in disk florets; coloration nearest RHS N200A.

*Filaments*.—Fused together at apex, 2.0 mm to 3.0 mm long and less than 0.2 mm diameter, filament coloration translucent to nearest RHS 155C.

*Pollen*.—Only found in disk florets; color nearest RHS 17B.

Gynoecium: In ray florets and disk florets; to about 7.0 mm long;

*Style*.—About 4.0 mm long and less than 0.5 mm diameter, split and curved at apical 1.0 mm; color nearest RHS 145C.

*Stigma*.—To about 1.5 mm long and less than 0.5 mm diameter; color nearest RHS 9C.

Involucre: Made of about three layers of phyllaries; to 2.8 cm across and 0.6 cm tall;

Phyllaries: Lanceolate; glabrous; margin entire and transparent; apex acute; base truncate; to about 72 per head arranged in about three imbricate rows; 8.0 mm long and 3.0 mm wide;

Phyllaries color: Adaxial center lustrous, nearest RHS 137A, margin transparent, region between margin and center nearest RHS N199B; abaxial center nearest RHS 146A, margin transparent, region between center and margin nearest RHS N199B;

Fruit: Achene, pointed at base and rounded at distal end with longitudinal color striations nearest RHS N200A and lighter than RHS 155D; about 3 to 4 mm long and 1.5 mm across;

*Leucanthemum* 'Marshmallow' grows best with adequate moisture but can tolerate some dryness once established. Vernalization is not required for flowering but is beneficial. The new plant is tolerant of high temperatures of at least 36° and cold hardy to at least USDA zone 5 as well as strong wind and rain. Other disease or pest resistance beyond that common to Shasta daisy has not been observed.

I claim:

1. The new and distinct Shasta daisy plant *Leucanthemum* 'Marshmallow' as herein shown and described.

* * * * *